(12) United States Patent
Khatri et al.

(10) Patent No.: US 9,090,560 B2
(45) Date of Patent: Jul. 28, 2015

(54) PROCESS FOR MICROWAVE ASSISTED SYNTHESIS OF N-METHYL PYRROLIDONE

(71) Applicant: Council of Scientific & Industrial Research, Rafi Marg, New Delhi (IN)

(72) Inventors: Praveen Kumar Khatri, Dehradun (IN); Suman Lata Jain, Dehradun (IN); Alok Kumar Chaterjee, Dehradun (IN); Sain Bir, Dehradun (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/477,075

(22) Filed: Sep. 4, 2014

(65) Prior Publication Data

US 2015/0065731 A1    Mar. 5, 2015

(30) Foreign Application Priority Data

Sep. 4, 2013 (IN) .......................... 2617/DEL/2013

(51) Int. Cl.
*C07D 207/267* (2006.01)
*C07D 207/404* (2006.01)

(52) U.S. Cl.
CPC ........ *C07D 207/404* (2013.01); *C07D 207/267* (2013.01)

(58) Field of Classification Search
CPC .................................................. C07D 207/267
USPC ....................................................... 548/554
See application file for complete search history.

(56) References Cited

U.S. PATENT DOCUMENTS

| | | |
|---|---|---|
| 3,073,843 A | 1/1963 | Buc et al. |
| 3,080,377 A | 3/1963 | Liao et al. |
| 3,092,638 A | 6/1963 | Liao et al. |
| 3,109,005 A | 10/1963 | Lidov et al. |
| 3,198,808 A | 8/1965 | Walldorf et al. |
| 3,448,118 A | 6/1969 | Chichery et al. |
| 3,681,387 A | 8/1972 | Hollstein et al. |
| 4,263,175 A | 4/1981 | Pesa et al. |
| 4,404,391 A | 9/1983 | Meyer et al. |
| 4,780,547 A | 10/1988 | Zur Hausen et al. |
| 4,814,464 A | 3/1989 | Olsen |
| 4,841,069 A | 6/1989 | Olsen |
| 4,965,370 A | 10/1990 | Goetz et al. |
| 4,973,708 A | 11/1990 | Digenis et al. |
| 5,101,045 A | 3/1992 | Koehler et al. |
| 5,157,127 A | 10/1992 | Weyer et al. |
| 6,248,902 B1 | 6/2001 | Bertola |
| 6,348,601 B2 | 2/2002 | Ohlbach et al. |
| 6,987,191 B1 | 1/2006 | Bertola et al. |

OTHER PUBLICATIONS

Jumbam et al. (S. Afr. J. Chem., 2011, 64-42-43).*
Frye, et al. 2005 "Novel multistep process for production of N-methyl-2-pyrrolidone from renewable resources" on the internet at: iic.pnnl.gov/abstracts/nacs/o_113.pdf (in one page).

* cited by examiner

*Primary Examiner* — Robert Havlin
(74) *Attorney, Agent, or Firm* — Knobbe, Martens, Olson & Bear, LLP

(57) ABSTRACT

The present invention relates to a process for microwave assisted synthesis of N-methyl pyrrolidone (NMP). Particularly the process relates to the synthesis of N-methyl succinimide or corresponding analogs by using microwave irradiation which on hydrogenation in the presence of a hydrogenating catalyst gives N-methyl pyrrolidone. Compared to the conventional heating microwave process requires less energy inputs and reduces the reaction time drastically from 5-6 h to 2-5 min.

12 Claims, 2 Drawing Sheets

PROCESS FOR MICROWAVE ASSISTED SYNTHESIS OF N-METHYL PYRROLIDONE

FIELD OF THE PRESENT INVENTION

The present invention relates to a process for microwave assisted synthesis of N-methyl pyrrolidone.

BACKGROUND OF THE PRESENT INVENTION

The N-methyl pyrrolidone (called "NMP" for short), is one of the important industrial chemicals and widely applied in various fields such as petroleum chemical industry, agricultural chemical, medicine and electronic material.

In the prior art, the N-methyl pyrrolidone is obtained through heating, pressurization and dehydration of N-methyl-4-hydroxyl butyryl amide which is produced by the reaction of the gamma-butyrolactone and methylamine, and this is the only industrial process for producing N-methyl pyrrolidone, and used by corporations such as American GAF, German BASF and the Japanese Mitsubishi and so on for mass production. Since the difference between boiling points of the NMP and raw material gamma-butyrolactone is only 2 degree C., it is very difficult to separate the two reagents above by method of rectification.

The U.S. Pat. No. 4,965,370 and the European patent EP 346086A2 disclosed the method for preparing highly purified NMP by adding alkaline metal or alkaline metal salt to reduce the acidic compound content of the reaction solution of NMP. The high purity NMP was then obtained by distillation.

Japanese patent JP06-279401A and JP08-109167A both use repeated distillation to obtain high purity NMP. However, it is difficult to produce NMP on the large scale through using the methods above because of their high cost and high energy consumption, difficult process control and high risk.

The prior art includes the preparation of N-substituted 2-pyrrolidones from a large number of compounds by catalytic hydrogenation. The starting compounds concerned are mixtures of a primary amine (II) and maleic anhydride (DE-A 4,018,243, U.S. Pat. No. 3,109,005) or fumaric acid, maleic acid, succinic acid, functional derivatives of these acids such as succinic anhydride, or amides, imides derived from the reaction of II with the acids as mentioned above, all of which can be hydrogenated to produce N-substituted 2-pyrrolidones (U.S. Pat. No. 5,434,273). Irrespective of the nature of these starting materials the reaction mixtures obtained after hydrogenation are worked up by distillation to obtain the pure product.

Olsen, in U.S. Pat. No. 4,814,464 described process for making N-alkylpyrrolidones from a maleic derivative or a succinic derivative which involves conversion of succinic anhydride to N-alkylsuccinimide by ammonolysis-alkylation with alkanol and ammonia, and catalytically reducing the resulting N-alkylsuccinimide to the N-alkylpyrrolidone.

Olsen, in U.S. Pat. No. 4,841,069 described reactions of succinic anhydride, methanol, ammonia and hydrogen to obtain NMP. Olsen described a reaction between succinic anhydride, methanol, and ammonia, and 700 psig of hydrogen in presence of 5% palladium on carbon catalyst, were heated 21 hrs at 290° C. with stirring. Olsen reported that 100% of the succinic anhydride was converted with 60% selectivity to N-methyl succinimide and 30% selectivity to N-methyl pyrrolidone.

Olsen, in U.S. Pat. No. 4,814,464 described the similar ammonolysis-alkylation reactions in which a succinic derivative such as the anhydride, acid or diester is reacted with ammonia and a $C_1$ to $C_4$ alkanol to give corresponding N-alkylsuccinimide. The N-alkylsuccinimide can be reduced catalytically with hydrogen either continuously or batch-wise to obtain NMP.

Koehler et al., in U.S. Pat. No. 5,101,045 described a process for the preparation of N-substituted pyrrolidones by catalytic hydrogenation of maleic anhydride, maleic acid and/or fumaric acid in the presence of ammonia, a primary alcohol and a modified cobalt oxide catalyst. In Example 3 of the patent, it has been stated that 75 ml of a 45% aqueous diammonium maleate solution and 75 ml methanol were hydrogenated for 42 hours at 230 C. in the presence of 10 g of a modified cobalt oxide catalyst to produce NMP in 89% yield.

Several patents such as U.S. Pat. No. 3,080,377; U.S. Pat. No. 3,198,808; U.S. Pat. No. 3,681,387 and U.S. Pat. No. 4,263,175 described the hydrogenation of succinic acid or anhydride in the presence of ammonia to yield 2-pyrrolidones. Catalysts used for the said synthesis include, the palladium on carbon, ruthenium on carbon, ruthenium on alumina, and cobalt oxide.

Chichery et al., in U.S. Pat. No. 3,448,118; Weyer et al. in U.S. Pat. Nos. 5,157,127 and 5,434,273 disclosed methods of making N-substituted pyrrolidones in which succinic acid or anhydride or the like is hydrogenated in the presence of a primary amine.

Jr. Fyre in EP patent 2210877 A1 described a process for the synthesis of pyrrolidone especially NMP via hydrogenation of succinic anhydride, succinic acid, or the like in presence of a catalyst comprising two metals in aqueous conditions.

All the aforementioned processes have the disadvantage either that the synthesis of intermediate imide requires longer reaction time, high reaction temperature or that the poor yield of the product. Further the aqueous nature of the methylamine provides unsatisfactorily low yields and impure product.

Synthesis of cyclic imides from the reaction of cyclic anhydride with hydroxylamine hydrochloride using 4-N,N-dimethylaminopyridine (DMAP) as catalyst under microwave irradiation is reported in the literature (*Molecules,* 2008, 13, 157-169). However, this method is associated with some drawbacks such as requirement of catalyst, higher reaction temperature and using only hydroxylamine hydrochloride.

Workers at the Pacific Northwest National Lab (PNNL) have developed a simple multi-step process involving both catalytic and non catalytic reactions which converts succinic acid into NMP. The developed process consisted two essential steps, i.e. non-catalytic (thermal) conversion of diammonium succinate (DAS) and methanol to n-methyl succinimide (NMS) followed by hydrogenation of the NMS to NMP. They have reported rhodium based catalysts for the hydrogenation of N-methylsuccinimide to N-methyl-2-pyrrolidone, which are highly expensive.

The drawbacks of the hitherto known processes such as higher energy inputs, longer reaction times, high temperature, lower conversion and poor selectivity, evident the necessity for the development of an improved process for the synthesis of N-methyl pyrrolidone.

It has been well established that using microwave irradiation reduces the reaction time as compared to the traditional synthesis by several hours, which allows the preparation to be achieved by using less energy inputs and shorter reaction time.

OBJECTIVE OF THE PRESENT INVENTION

The main object of the present invention is to provide a process for microwave assisted synthesis of N-methyl pyrrolidone (NMP), which obviates the drawbacks of the hitherto known prior art as detailed above.

Another objective of the present invention is to provide a process for the synthesis of N-methyl pyrrolidone (I) by the reaction of maleic acid, maleic anhydride or succinic acid, succinic anhydride or their analogues derivatives (compounds III) with anhydrous methylamine (IV) under microwave irradiation to give intermediate amides or imides, which on subsequent hydrogenation in the presence of a noble metal based hydrogenating catalyst followed by the isolation and purification of I by distillation from the reaction mixture.

Yet another objective of the present invention is to perform the reaction in the absence of solvent under microwave irradiation, which requires less energy inputs; therefore, it represents a "greener" preparation than the traditional synthesis of intermediate imide.

Yet another objective of the present invention is to use the non-aqueous methylamine under microwave irradiation; therefore the process provides an easy handling, energy efficient and fast synthesis of intermediate imide.

Yet another objective of the present invention is to provide a process for the preparation of pure NMP (>99% purity).

SUMMARY OF THE INVENTION

Accordingly, the present invention provides a process for synthesis of N-methyl pyrrolidone, said process comprising the steps of:

(a) reacting a dicarboxylic acid or corresponding anhydride with non-aqueous methylamine with a molar ratio in the range 1:1 to 1:10 in solid state using microwave irradiation in the range of 600-900 W for a period of 1 to 10 minutes to obtain an intermediate N-methyl imide;

(b) separating and purifying the intermediate N-methyl imide thus formed;

(c) converting the intermediate N-methyl imide to N-methyl pyrrolidone.

In one embodiment of the present invention said dicarboxylic acid or anhydride is selected from the group consisting of maleic acid, maleic anhydride, succinic acid or succinic anhydride and their analogous.

In an embodiment of the present invention said non aqueous methylamine is selected from the group consisting of anhydrous methylamine, methylamine in THF or methylamine hydrochloride.

In an embodiment of the present invention, an organic solvent is used for separating the intermediate N-methyl imide thus formed.

In another embodiment of the present invention, an organic solvent is selected from the group consisting of chloroform, ethyl acetate, dichloromethane, and toluene.

In another embodiment of the present invention, purifying the intermediate N-methyl imide comprises subjecting the intermediate N-methyl imide to a crystallization process.

In another embodiment of the present invention, conversion of intermediate N-methyl imide to N-methyl pyrrolidone comprises hydrogenating intermediate N-methyl imide in presence of a solid state hydrogenating catalyst at a temperature in the range of 250 to 500° C., a pressure in the range of 30 to 70 bar and a time period in the range of 3 to 10 hours.

In another embodiment of the present invention the solid hydrogenating catalyst is supported metal based catalyst.

In another embodiment of the present invention metal is selected from the group consisting of Pd, Pt, Cu, Rh or Nickel.

In another embodiment of the present invention the hydrogenating catalyst contains 0.1% to 20% of the metal by weight.

In another embodiment of the present invention support material is selected from the group consisting of carbon, alumina, titania, zirconia.

In another embodiment of the present invention yield of N-methyl pyrrolidone is in the range of 85-93%.

BRIEF DESCRIPTION OF DRAWINGS

FIG. 1 1H NMR spectra of NMS
FIG. 2 13C NMR spectra of NMS

DETAILED DESCRIPTION OF THE INVENTION

Figure 1:
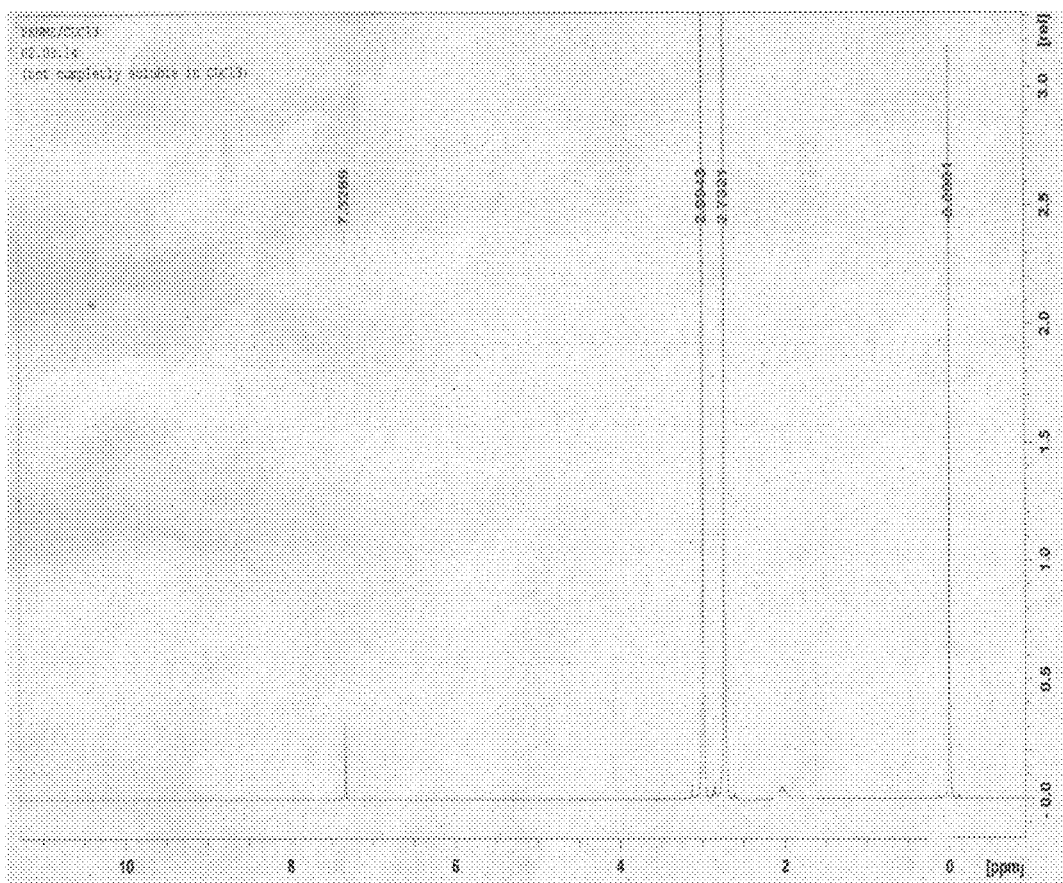
Figure 2:
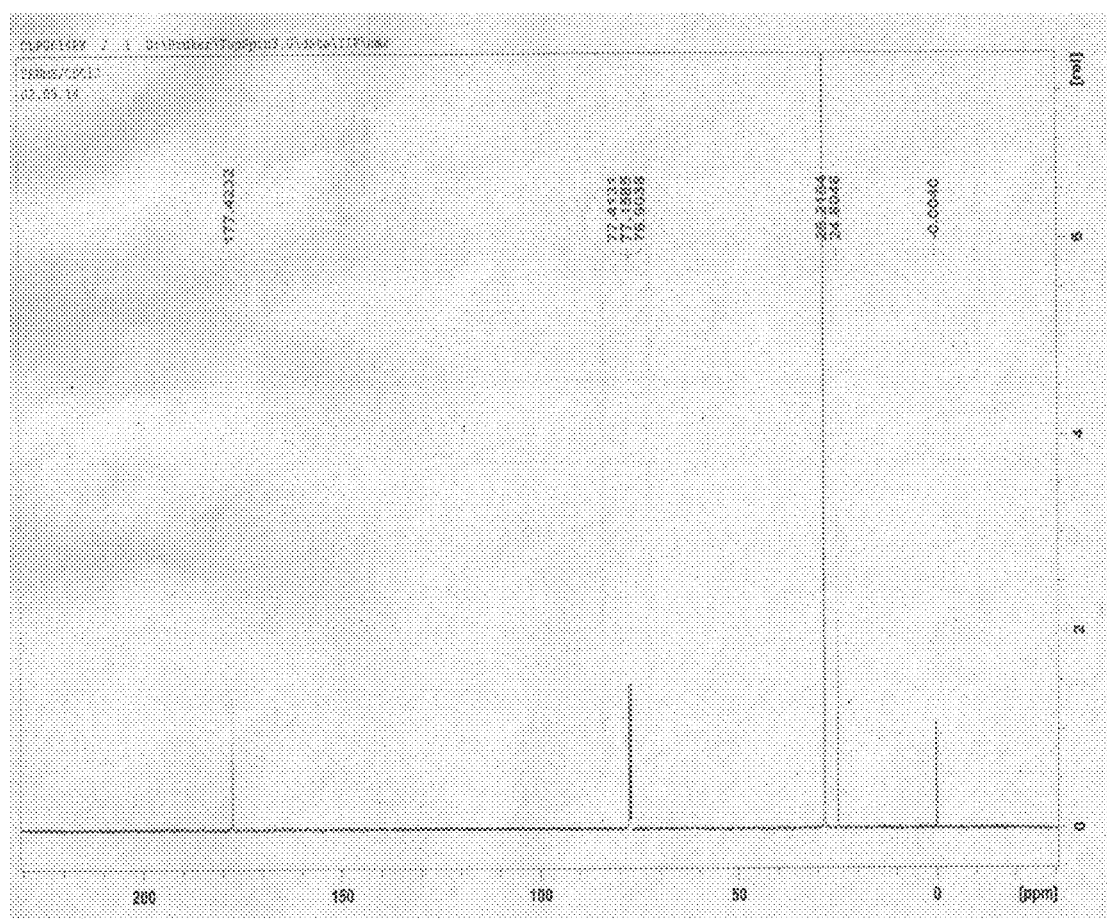

In the present invention, the reaction between dicarboxylic acids or their anhydrides and non-aqueous methylamine in a molar ratio range 1:1 to 1:10 is performed in the solid state by the microwave irradiation for 1 to 5 minutes. The acceleration of a reaction by microwave exposure results from material-wave interactions leading to thermal effect (which may be easily estimated by temperature measurements) and specific (i.e., not purely thermal) effects. A combination of these two contributions could be responsible for the observed effects. The intermediate N-methyl imide may be isolated from the above mentioned reaction mixture by different separation methods such as distillation, extraction, precipitation, filtration preferably by extraction with an organic solvent and purified by a number of methods such as chromatography, crystallization, decanting, sublimation, extraction and distillation, preferably by crystallization. Then the intermediate is reduced to N-methyl pyrrolidone (I). Reduction of the intermediate can be performed by different methods such as electrochemical reduction of succinimide, reduction with nascent hydrogen, hydrogenation in the presence of a catalyst or in the presence of reducing agents.

Hydrogenation may also be performed in the presence of hydrogen and ammonia with a hydrogenating metal selected from the group consisting of cobalt, nickel, ruthenium, palladium and platinum at a temperature of 60-350° C. and a pressure of about 50-10,000 p.s.i.g.

The catalysts for hydrogenation may comprise at least one metal selected from the group consisting of Fe, Ni, Pd, Sn, Pt, Co, Re, Rh, Ir, Os, Ag, Au, Ru, Zr, and Cu supported on a support such as a carbon, alumina, and silica. A different type of catalysts comprise a first metal, an oxide material comprising a second metal and a carbon support, the second metal comprising at least one member of the group consisting of Zr, Hf, Ta, Nb, Mo, W, Zn, Sn, V, Fe, U and Th.

Some reducing agents can also be employed for hydrogenation of succinimide such as lithium aluminium hydride and lithium borohydride.

Further, a number of solvents such as dioxane, methanol, ethanol and butanol are known to be used in the hydrogenation of succinimide. However, the present process aims at a solvent less hydrogenation of succinimide to reduce the consumption of energy. Therefore, it is preferable to perform the hydrogenation by subjecting to hydrogenation in a high pressure autoclave in the presence of a hydrogenation catalyst for 3 to 10 h to yield N-methyl pyrrolidone (I), which is obtained by the distillation from the resulting reaction mixture. As stated above, the invention provides a process for microwave assisted synthesis of N-methyl pyrrolidone by reacting dicarboxylic acid or anhydride and methyl amine hydrochloride in solid state under microwave irradiation to give intermediate N-methyl imide which on subsequent hydrogenation provides N-methyl pyrrolidone.

Following are the examples given to further illustrate the invention and should not be construed to limit the scope of the present invention.

Example 1

Succinic anhydride (4 mmol) and methylamine hydrochloride (4.5 mmol) were charged into a 25 ml round bottomed flask and placed in a milestone microwave reactor fitted with a condenser. The mixture was irradiated at 110° C. by an energy input of 850 W for 1 minute. The reaction mixture was being cooled to room temperature and extracted with ethyl acetate. The combined organic layer was dried over anhydrous sodium sulphate and concentrated under reduced pressure. The crude product was purified by crystallization with n-hexane to yield pure N-methyl succinimide (NMS) in 90% yield. The product was fully characterized by NMR ($^1$H and $^{13}$C) and gas chromatography by comparing the data with commercially available NMS of Aldrich as standard.

Example 2

Succinic anhydride (4.0 mmol) and methylamine hydrochloride (4.5 mmol) were charged into a 25 ml round bottomed flask and placed in a milestone microwave reactor fitted with a condenser. The mixture was irradiated at 100° C. by an energy input of 900 W for 1 minute. The reaction mixture was being cooled to room temperature and extracted with ethyl acetate. The combined organic layer was dried over anhydrous sodium sulphate and concentrated under reduced pressure. The crude product was purified by crystallization with n-hexane to yield pure N-methyl succinimide (NMS) in 67% yield.

Example 3

Succinic anhydride (4.0 mmol) and methylamine hydrochloride (4.5 mmol) were charged into a 25 ml round bottomed flask and placed in a milestone microwave reactor fitted with a condenser. The mixture was irradiated at 125° C. by an energy input of 900 W for 1 minute. The reaction mixture was being cooled to room temperature and extracted with ethyl acetate. The combined organic layer was dried over anhydrous sodium sulphate and concentrated under reduced pressure. The crude product was purified by crystallization with n-hexane to yield pure N-methyl succinimide (NMS) in 87% yield.

Example 4

Succinic anhydride (4.0 mmol) and methylamine hydrochloride (4.5 mmol) were charged into a 25 ml round bottomed flask and placed in a milestone microwave reactor fitted with a condenser. The mixture was irradiated at 110° C. by an energy input of 900 W for 1 minute. The reaction mixture was being cooled to room temperature and extracted with ethyl acetate. The combined organic layer was dried over anhydrous sodium sulphate and concentrated under reduced pressure. The crude product was purified by crystallization with n-hexane to yield pure N-methyl succinimide (NMS) in 90% yield.

Example 5

Effect of Reaction Time

Succinic anhydride (4.0 mmol) and methylamine hydrochloride (4.5 mmol) were charged into a 25 ml round bottomed flask and placed in a milestone microwave reactor fitted with a condenser. The mixture was irradiated at 110° C. by an energy input of 850 W for three minute. The reaction mixture was being cooled to room temperature and extracted with ethyl acetate. The combined organic layer was dried over anhydrous sodium sulphate and concentrated under reduced pressure. The crude product was purified by crystallization with n-hexane to yield pure N-methyl succinimide (NMS) in 87% yield.

Example 6

Reaction was Carried Out by Using Dimethylamino Pyridine (DMAP) Catalyst

Succinic anhydride (4.0 mmol) and methylamine hydrochloride (4.5 mmol) and DMAP (0.5 mmol) were charged into a 25 ml round bottomed flask and placed in a milestone microwave reactor fitted with a condenser. The mixture was irradiated at 80° C. by an energy input of 700 W for three minutes. The reaction mixture was being cooled to room temperature and extracted with ethyl acetate. The combined organic layer was dried over anhydrous sodium sulphate and concentrated under reduced pressure. The crude product was purified by crystallization with n-hexane to yield pure N-methyl succinimide (NMS) in 45% yield.

Example 7

Succinic anhydride (4.0 mmol) and methylamine hydrochloride (4.5 mmol) and DMAP (0.5 mmol) were charged into a 25 ml round bottomed flask and placed in a milestone microwave reactor fitted with a condenser. The mixture was irradiated at 100° C. by an energy input of 700 W for two minutes. The reaction mixture was being cooled to room temperature and extracted with ethyl acetate. The combined organic layer was dried over anhydrous sodium sulphate and concentrated under reduced pressure. The crude product was purified by crystallization with n-hexane to yield pure N-methyl succinimide (NMS) in 78% yield.

Example 8

Succinic anhydride (4.0 mmol) and methylamine hydrochloride (4.5 mmol) and DMAP (0.5 mmol) were charged into a 25 ml round bottomed flask and placed in a milestone microwave reactor fitted with a condenser. The mixture was irradiated at 100° C. by an energy input of 700 W for three minutes. The reaction mixture was being cooled to room temperature and extracted with ethyl acetate. The combined organic layer was dried over anhydrous sodium sulphate and concentrated under reduced pressure. The crude product was purified by crystallization with n-hexane to yield pure N-methyl succinimide (NMS) in 82% yield.

Example 9

Succinic anhydride (4.0 mmol) and methylamine hydrochloride (4.5 mmol) and DMAP (0.5 mmol) were charged into a 25 ml round bottomed flask and placed in a milestone microwave reactor fitted with a condenser. The mixture was irradiated at 125° C. by an energy input of 700 W for three minutes. The reaction mixture was being cooled to room temperature and extracted with ethyl acetate. The combined organic layer was dried over anhydrous sodium sulphate and concentrated under reduced pressure. The crude product was purified by crystallization with n-hexane to yield pure N-methyl succinimide (NMS) in 86% yield.

Example 10

Hydrogenation of N-methyl Succinimide

A 100 cc stainless steel high pressure reactor was charged with N-methyl succinimide (0.5 g; 4.24 mmol), distilled water (15 ml) and 10% Pd on activated charcoal (0.1 g) catalyst. The reactor was pressurized with 40 bar $H_2$ pressure and heated at 250° C. for 6 h. The reactor was being cooled to room temperature and excess $H_2$ released gently. Catalyst was recovered by filtration and the resulting filtrate was concentrated under reduced pressure to give a colorless liquid NMP. The conversion of NMS was found to be 93% and selectivity >99% for NMP, as analyzed by GC analysis.

Example 11

A 100 cc stainless steel high pressure reactor was charged with N-methyl succinimide (0.5 g; 4.24 mmol), distilled water (15 ml) and 10% Pd on activated charcoal (0.1 g) catalyst. The reactor was pressurized with 40 bar $H_2$ pressure and heated at 230° C. for 3 h. The reactor was being cooled to room temperature and excess $H_2$ released gently. Catalyst was recovered by filtration and the resulting filtrate was concentrated under reduced pressure to give a colorless liquid NMP. The conversion of NMS was found to be 56% and selectivity >99% for NMP, as analyzed by GC analysis.

Advantages of the Present Invention

The present process is uniformly applicable for a wide variety of dicarboxylic acid or their analogous like maleic acid, succinic acid or their derivatives.

The present invention describes for first time the use of microwave heating for the synthesis of N-methyl imide intermediate from the reaction of dicarboxylic acid or anhydride with methyl amine.

The present invention described for the first time the use of methyl amine hydrochloride as the non-aqueous methyl source which is easy in handling and safe.

In the present invention, compared to the conventional heating microwave irradiation does not have any loss in energy and is economically favored.

In the present invention, hydrogenation of the intermediate N-methyl imide can be performed in the presence of conventional hydrogenating catalyst.

In the present invention, the yield of the final product i.e. N-methyl pyrrolidone is obtained >97% with the purity 98% or more.

What is claimed is:

1. A process for synthesis of N-methyl pyrrolidone, said process comprising the steps of:
   (a) reacting a dicarboxylic acid or corresponding anhydride with non-aqueous methylamine with a molar ratio in the range 1:1 to 1:10 in the solid state using microwave irradiation in the range of 600-900 W for a period of 1 to 10 minutes to obtain an intermediate N-methyl imide;
   (b) separating and purifying the intermediate N-methyl imide thus formed; and
   (c) converting the intermediate N-methyl imide to N-methyl pyrrolidone.

2. The process according to claim 1, wherein said dicarboxylic acid or anhydride is selected from the group consisting of maleic acid, maleic anhydride, succinic acid, succinic anhydride and an analog thereof.

3. The process according to claim 1, wherein said non aqueous methylamine is selected from the group consisting of anhydrous methylamine, methylamine in THF and methylamine hydrochloride.

4. The process according to claim 1, wherein an organic solvent is used for separating the intermediate N-methyl imide thus formed.

5. The process according to claim 4, wherein the organic solvent is selected from the group consisting of chloroform, ethyl acetate, dichloromethane and toluene.

6. The process according to claim 1, wherein purifying the intermediate N-methyl imide comprises subjecting the intermediate N-methyl imide to a crystallization process.

7. The process according to claim 1, wherein converting the intermediate N-methyl imide to N-methyl pyrrolidone comprises hydrogenating intermediate N-methyl imide in the presence of a solid state hydrogenating catalyst at a temperature in the range of 250 to 500° C., a pressure in the range of 30 to 70 bar and a time period in the range of 3 to 10 hours.

8. The process according to claim 7, wherein the solid hydrogenating catalyst is a supported metal based catalyst.

9. A process according to claim 8, wherein the metal is selected from the group consisting of Pd, Pt, Cu, Rh and Nickel.

10. A process according to claim 8, wherein the hydrogenating catalyst contains 0.1% to 20% of the metal by weight.

11. A process according to claim 8, wherein a support material in the supported metal based catalyst is selected from the group consisting of carbon, alumina, titania and zirconia.

12. A process according to claim 8, wherein a yield of N-methyl pyrrolidone is in the range of 85-93%.

* * * * *